(12) United States Patent
Wiseman et al.

(10) Patent No.: US 8,423,104 B2
(45) Date of Patent: Apr. 16, 2013

(54) HAEMOZOIN DETECTION

(75) Inventors: Paul W. Wiseman, Montréal (CA);
Jonathan Belisle, Montréal (CA);
Santiago Constantino, Montréal (CA);
Scott D. Bohle, Dorval (CA); Elias George, Chomedey (CA); Marie-Josée Bellemare, La Prairie (CA); Mara Leimanis, Pointe Claire (CA)

(73) Assignee: McGill University, Montreal, Quebec (CA)

( * ) Notice: Subject to any disclaimer, the term of this patent is extended or adjusted under 35 U.S.C. 154(b) by 370 days.

(21) Appl. No.: 12/669,161

(22) PCT Filed: Jul. 16, 2008

(86) PCT No.: PCT/CA2008/001314
§ 371 (c)(1),
(2), (4) Date: Jun. 11, 2010

(87) PCT Pub. No.: WO2009/009899
PCT Pub. Date: Jan. 22, 2009

(65) Prior Publication Data
US 2011/0204257 A1     Aug. 25, 2011

Related U.S. Application Data

(60) Provisional application No. 60/929,863, filed on Jul. 16, 2007.

(51) Int. Cl.
*A61B 5/00*     (2006.01)
(52) U.S. Cl.
USPC ......................................................... 600/322

(58) Field of Classification Search .................... 600/322
See application file for complete search history.

(56) References Cited

U.S. PATENT DOCUMENTS

| | | | |
|---|---|---|---|
| 6,222,456 B1 * | 4/2001 | Tice | 340/630 |
| 6,961,599 B2 * | 11/2005 | Lambert et al. | 600/318 |
| 7,108,970 B2 | 9/2006 | Levinson | |
| 7,567,596 B2 * | 7/2009 | Dantus et al. | 372/30 |
| 2005/0042698 A1 * | 2/2005 | Demirev et al. | 435/7.22 |
| 2008/0170218 A1 * | 7/2008 | Dantus et al. | 356/39 |

FOREIGN PATENT DOCUMENTS

WO     2008/056171     5/2008

OTHER PUBLICATIONS

Oron, et al., Harmonic generation with temporally focused ultrashort pulses, J. Opt. Soc. Am. B, vol. 22, No. 12, Dec. 2005.*
Yelin, D., et al., Third-harmonic microscopy with a titanium-sapphire laser, Appl. Phys. B 74 (Suppl.), S97-S101 (2002).*
International Preliminary Report on Patentability for PCT/CA2008/001314 (mailed Jan. 28, 2010).

(Continued)

*Primary Examiner* — Rodney Fuller
(74) *Attorney, Agent, or Firm* — Perley-Robertson, Hill & McDougall LLP (57) ABSTRACT

A system for detecting haemozoin in a sample, said system including a light source for exciting the sample with an optical signal to generate a non-linear optical response, and a detector for detecting the generated non-linear optical response from the excited sample. A method for detecting haemozoin in a sample, the method including exciting the sample with an optical signal to generate a non-linear optical response from the sample, and detecting the emitted non-linear optical signal from the excited sample.

10 Claims, 4 Drawing Sheets

OTHER PUBLICATIONS

Written Opinion for PCT/CA2008/001314 (mailed Oct. 7, 2008).

Belisle, J. et al., "Sensitive Detection of Malaria Infection by Third Harmonic Generation Imaging," *Biophysical Journal: Biophysical Letters*, pp. L26-L28 (Dec. 7, 2007).

Baena, J. et al., "Raman spectroscopy in chemical bioanalysis," *Current Opinion in Chemical Biology*, vol. 8, No. 5, pp. 534-539 (2004).

Clay, G. et al., "Spectroscopy of third-harmonic generation: evidence for resonances in model compounds and ligated hemoglobin," Manuscript ID 64600 Prepared for Publication in the Journal of the Optical Society of America (JOSA-B). 51 pages (Nov. 16, 2005).

International Search Report for PCT/CA2008/001314 (mailed Oct. 7, 2008).

Yelin, D. et al., "Laser scanning third-harmonic-generation microscopy in biology," *Optics Express*, vol. 5, No. 8, pp. 169-175 (Oct. 11, 1999).

\* cited by examiner

HAEMOZOIN DETECTION

CROSS REFERENCE TO RELATED APPLICATIONS

This is the U.S. National Stage of International Application No. PCT/CA2008/001314, filed Jul. 16, 2008, which was published in English under PCT Article 21(2), which in turn claims the benefit of U.S. Provisional Application No. 60/929,863, filed Jul. 16, 2007. The provisional application is incorporated herein in its entirety.

FIELD OF THE INVENTION

The present invention generally relates to a system and a method for detecting the presence of haemozoin in a sample, for example as a marker of malaria infection in blood or tissue or the like.

BACKGROUND OF THE INVENTION

Malaria is an insect-borne disease that is widespread in tropical and subtropical regions, including parts of Asia, Africa and the Americas. As well as its human cost, malaria also has an economic impact particularly in developing countries where the disease is endemic. Malaria infection rates are also rising in industrial countries, such as the USA and Canada, due to increased international travel, movement of refugees, immigration and migrant workers.

Four parasites are thought to be responsible for malaria: *plasmodium falciparum, plasmodium vivax, plasmodium ovale* and *plasmodium malariae*. The most common and serious form of the disease is caused by *plasmodium falciparum*. Malaria parasites are transmitted by female mosquitoes when they bite a victim. The parasites multiply within the victim's red blood cells causing symptoms such as fever, shivering, vomiting, anaemia, convulsions, and eventually coma and death if left untreated. At the early activated (trophozoite) stage, the malarial parasites are inside red blood cells and digest the haemoglobin of the red blood cells to synthesize amino acids to multiply. Heme is produced as a metabolic product of the degradation of haemoglobin and as the heme exhibits a strong cytotoxic effect to the malarial parasite, the malarial parasite converts the heme into haemozoin, a non-toxic polymer, which the malarial parasite deposits into food vacuoles in its body. The haemozoin is in the form of crystals comprising a hydrogen bonded chain of dimers formed by iron carboxylate bonds.

Due to the non-specific clinical symptoms of malaria, clinical diagnosis of malaria can be unreliable. Therefore, accurate diagnosis of malaria in a victim relies on testing the victim's blood. Blood testing methods for the detection of malaria include: 1) DNA/RNA staining methods e.g. Giemsa staining, Fluorescent staining, QBC®; 2) Antigen detection methods; 3) Automated malaria pigment detection methods; and 4) molecular methods (Hanscheid T. (1999) Diagnosis of malaria: a review of alternatives to conventional microscopy. *Clin. Lab. Haem.*, 21, pp. 235-245).

Giemsa staining is the most commonly used detection method and involves the staining of blood films or smears to detect the DNA/RNA of the malaria parasite. The main advantage of this method is its low cost and the fact that parasitaemia levels as low as 0.0001% can be detected. The most significant drawback of this detection method is that it relies on the examination of blood samples by a technician using an optical microscope. Thus the proper training of technicians is required. Also, the quality and accuracy of the diagnosis relies on the skills and experience of the technician. Moreover, the process for identifying parasites by light microscopy is time consuming and multiple tests cannot be performed simultaneously. Furthermore, the processes of smearing, fixing and staining the blood prior to its analysis require specific equipment and reagents which are prone to degradation.

Another staining approach is fluorescence tagging of DNA/RNA. As red blood cells (mature mammalian erythrocytes) do not contain DNA whereas malaria parasites do, nucleotide specific fluorescent dyes can be used to detect the presence of the malaria parasite. The most common dye employed is acridine orange (AO), but the method still relies on the careful examination of blood samples as well as technician skill and generally does not give better results than the Giemsa staining method.

The DNA/RNA staining approach can be further refined using an AO coated capillary, termed QBC® (quantitative buffy coat), which is centrifuged and examined. Although this approach improves the sensitivity of the DNA/RNA staining approach and can be automated, it requires additional material, equipment, training, is more costly and is not more sensitive than the Giemsa staining method. Therefore, it has the same drawbacks as the Giemsa staining method.

Antigen detection methods detect the presence of proteins specific to malaria and are the most common approach to rapid malaria testing. There are three common formats: dipstick, cartridge and cassette. These methods are suitable for use in remote areas as they do not require specific operator training. Advantageously, many tests can be performed simultaneously. One such antigen detection method is HRP-2 available from Parasight® which detects the presence of a particular histidine-rich protein specific to the malaria parasite using a dipstick approach. The sensitivity of this method is comparable to the staining methods, and the time per test is shorter so many tests can be carried out simultaneously. However, antigen detection methods are generally more expensive than the staining methods. Also, the tests provide just a negative or a positive result and therefore more detailed examination is necessary to confirm the diagnosis. Furthermore, degradation of the test reagents of antigen detection methods are accelerated under high temperature and humidity conditions, such as those found in regions of the world where malaria is endemic.

Automated pigment detection methods typically use an automated haemotology analyzer and have the advantage of not requiring a skilled technician to prepare samples and operate a microscope. One such method involves the detection of an abnormal monocyte population using the Cell-Dyn™ 3500 analyzer (Abbott-Diagnostics, Maidenhead, UK). The main problems with the automated pigment detection methods are that they are unable to detect parasitaemia levels and that an abnormal monocyte population is not specific to malaria.

Molecular methods include a polymerase chain reaction method which uses specific parasite genetic sequences and is the most sensitive technique of all the above-mentioned techniques. However, this method is very time consuming and the high cost per test does not make it suitable for individual diagnosis.

Despite the fact that many techniques exist to detect haemozoin to attempt to diagnose malaria, there is a need for an improved system, method or device.

SUMMARY OF THE INVENTION

The inventors have made the surprising and unexpected discovery that haemozoin has a strong non-linear optical response and that this can be exploited to detect the presence of haemozoin in samples such as blood, blood cells, tissue or any other media, to diagnose malaria or other diseases for which haemozoin may be a marker. Specifically, the inventors have made the surprising discovery that haemozoin produces a third harmonic signal when excited with an optical signal from a laser. The optical signal may be continuous but is preferably ultrashort laser pulses. By ultrashort it is meant laser pulses of a duration less than 1 nanosecond, typically in the picosecond to femtosecond timescales. This signal can be used for automated detection of malaria in blood, blood cells (defined as red and/or white blood cells), tissue or the like including an indication of parasitaemia levels. This signal can also be used to image the haemozoin. Advantageously, it has been discovered that the third harmonic signal generated by haemozoin has a large signal to noise ratio which facilitates its detection and which means that it can be detected whether it is within a cell or tissue or other tissue-like structures. The detection of haemozoin in blood, cells and tissues is also facilitated by the inventors discovery that there is no other detected third harmonic signal in blood and cells with such a signal to noise ratio.

From one aspect there is provided a system for detecting haemozoin in a sample, said system including a light source for exciting the sample with an optical signal to generate a non-linear optical response, and a detector for detecting the generated non-linear optical response from the excited sample. Preferably, the non-linear optical response is a third harmonic signal.

Preferably, the light source is a laser which is arranged to emit ultrashort pulses of infrared light. The timing between the pulses can be of any length of time. The optical signal can also be a continuous optical signal generated by a high intensity laser, for example.

If the detected signal is a third harmonic signal above a certain threshold, then haemozoin is present in the sample. The presence of haemozoin in the sample is an indication that the sample is infected with the malaria parasite. Therefore, the system can be used to detect malaria in a patient. Preferably, the light source is a laser which is arranged to emit ultrashort pulses of infrared light.

In one embodiment, the detector is a photomultiplier tube but can also be a photodiode or an avalanche photodiode. The system may further comprise an imaging device for imaging the sample. The imaging device may include a second photomultiplier tube and a processor for processing the signals from the photomultiplier tubes to provide an image of the detected haemozoin and the sample.

The system may further comprise a converger, such as a lens or mirrors, for focusing the optical signal on the sample. If a lens is used, it can be a single lens, an objective or an axicon, for example. The sample and the optical signal can be moveable relative to one another for exciting a plurality of areas of the sample. For example, if the sample is a sample of a patient's blood, the blood cells can be made to move relative to the incident optical signal to analyse the presence of haemozoin in different cells. A cell sorter could be used for this. Alternatively, the incident optical signal can move relative to the sample.

The system can be applied to in vitro or in vivo analysis of samples. Accordingly, for in vitro analysis, the system may include a sample holder and the sample can be a patient's blood or tissue. For in vivo analysis, the sample is a portion of the patient's anatomy which must be positioned proximate the optical signal and the detector.

Optionally, the system can further comprise an alert means connected to the detector for indicating the presence or absence of haemozoin in the sample. A processor may be needed to process the data from the detector to trigger the alter means. Therefore, the system may also include a processor for processing the detected signal.

The system may be configured to detect either the scattered or the backscattered third harmonic signal from the sample.

For portable applications, the light source and the detector can be housed in a housing. It will be appreciated that the system can be embodied as a device or an apparatus.

From another aspect, the invention also resides in a method for detecting haemozoin in a sample, the method including exciting the sample with an optical signal to generate a non-linear optical response from the sample, and detecting the emitted non-linear optical signal from the excited sample. Preferably, the non-linear optical signal is a third harmonic signal.

Preferably, the optical signal is ultrashort pulses of infrared light. The timing between the pulses can be of any length of time. However, the optical signal can also be a continuous signal generated by a high intensity laser, for example.

The method may include moving the sample and the optical signal relative to one another to excite a plurality of portions of the sample. For example, one cell at a time can be presented to the incident optical signal to analyse the presence of haemozoin in different cells.

Advantageously, the method includes indicating the presence or absence of haemozoin in the sample.

Therefore, the present invention reduces the difficulties and disadvantages of the aforesaid haemozoin and malaria detection methods and systems by providing a method and a system for detecting malaria which is faster than known non-automated techniques (e.g. the Giemsa staining method), and has minimal training requirements for its operation which eliminates the need for a trained technician and also eliminates subjectivity associated with technician operation. When compared to known automated techniques such as, for example, the QBC® DNA/RNA staining method, the antigen detection methods and the Cell-Dyn™ automated pigment detection method, the device, system and method of the present invention has a lower cost per test and improved sensitivity. Furthermore, no reagents are required in the present invention to detect malaria compared to other existing techniques. Advantageously, the system of the invention when embodied as a device can be portable for both bedside, hospital use, as well as field use such as in remote areas where malaria is prevalent. The system and method of the present invention can also be used to screen people returning from endemic countries, for blood donation for example.

The method and system of the present invention provides an ideal screening or diagnostic tool as an operator need not be a skilled technician. In fact, in one embodiment, the operator need only extract a blood drop from the patient, and operate the device or system to obtain information about the patient's blood e.g. positive or negative infection with malaria and/or the parasitaemia level.

By way of background, third harmonic generation is discussed below. Third Harmonic Generation (THG) is a material-dependent nonlinear optical effect that involves the conversion of three photons of the fundamental laser frequency within the focus of a laser beam into one emitted photon of frequency due to the third-order dielectric susceptibility of the medium. In nonlinear optics, the polarization is expressed as a power series in terms of electric field:

$$P(t) = \chi^{(1)} E(t) + \chi^{(2)} E^2(t) + \chi^{(3)} E^3(t) + \quad \text{Equation (1)}$$

where $\chi^{(2)}$ is the second order nonlinear susceptibility, $\chi^{(3)}$ is the third order nonlinear susceptibility, and so on. Consider a laser beam with the following electric field:

$$E(t) = Ee^{-i\omega t} + E^* e^{i\omega t} \quad \text{Equation (2)}$$

and that this beam is incident on a crystal or any material with a nonzero third-order susceptibility $\chi^{(3)}$. The third-order term in the nonlinear polarization from Equation 1 will become:

$$P^{(3)}(t) = 3\chi^{(3)}(E^2 E^* e^{-i\omega t} + E(E^*)^2 e^{i\omega t}) + \chi^{(3)}(E^3 e^{-3i\omega t} + (E^*)^3 e^{3i\omega t}). \quad \text{Equation (3)}$$

Figures 1, 2:
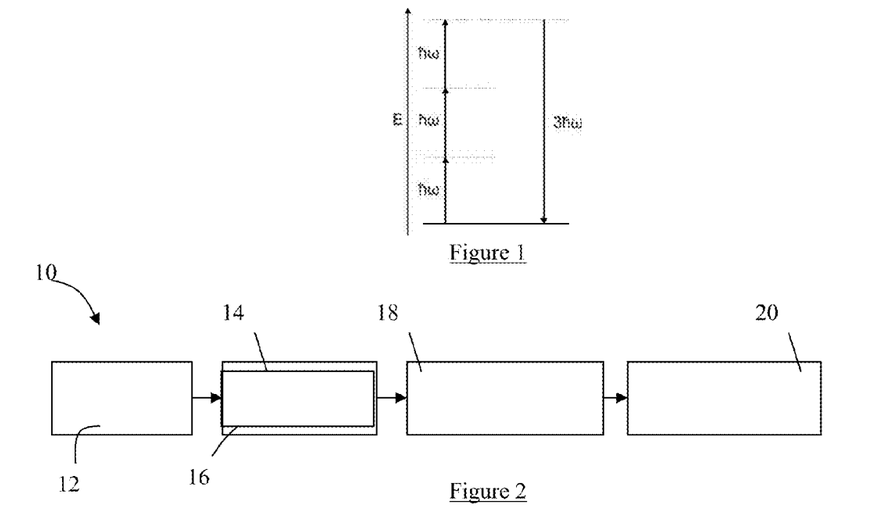
FIG. 1 is a Jablonski energy diagram of third harmonic generation.
FIG. 2 illustrates a system embodying the present invention.

The first term in Equation 3 does not contribute to third harmonic generation since its frequency is ω, but it adds a nonlinear contribution to the polarization at the frequency of the incident electric field. This also leads to a nonlinear contribution to the refractive index and explains self-focusing of light. The second term of frequency 3ω is responsible for the generation of third harmonic light. FIG. 1 shows a Jablonski energy diagram that illustrates third harmonic generation where three incident photons are annihilated to create a single photon of three times the incident frequency. The three upward arrows represent three incident photons each of energy ħω that are converted into one photon of emitted THG light of energy 3 ω represented by the downward arrow.

BRIEF DESCRIPTION OF THE DRAWINGS

Further aspects and advantages of the present invention will become better understood with reference to the description in association with the following drawings in which.

DETAILED DESCRIPTION OF THE INVENTION

Unless otherwise stated, the following definitions apply:

The singular forms "a", "an" and "the" include corresponding plural references unless the context clearly dictates otherwise.

As used herein, the terms "including", "comprising", "having", "containing", "involving" and variations thereof herein, are intended to mean that elements listed thereafter are required and that other elements may or may not be present.

As used herein, the term "blood cells" is intended to mean red blood cells or white blood cells.

As used herein, the term "third harmonic generation" is intended to mean an emitted non-linear optical response. By non-linear optical response it is meant that the emitted optical response does not scale linearly with the excitation intensity.

As used herein, the terms "victim" and "patient" are used interchangeably and are intended to mean humans and non-human mammals such as primates. In one example, the subject is a human.

As used herein, the term "sample" is intended to mean samples of blood, tissue or tissue-like structures taken from a patient for in vitro screening and also the patient's blood, tissue or tissue-like structures for in vivo screening.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting.

The invention includes a system 10 for detecting haemozoin in a sample. One application, which will be described below, is for the detection of malaria in blood, tissue and tissue-like structures using third harmonic generation of the haemozoin as a marker for malaria.

Referring initially to FIG. 2, the system 10 broadly comprises a light source 12, preferably a laser, for generating and emitting a light signal to be focused on a sample 14, the sample being optionally placed in a sample holder 16. There is also provided a detector 18 for detecting and collecting an emitted signal from the sample 14 and, optionally, a processor 20 for processing the emitted signal.

Figure 3:
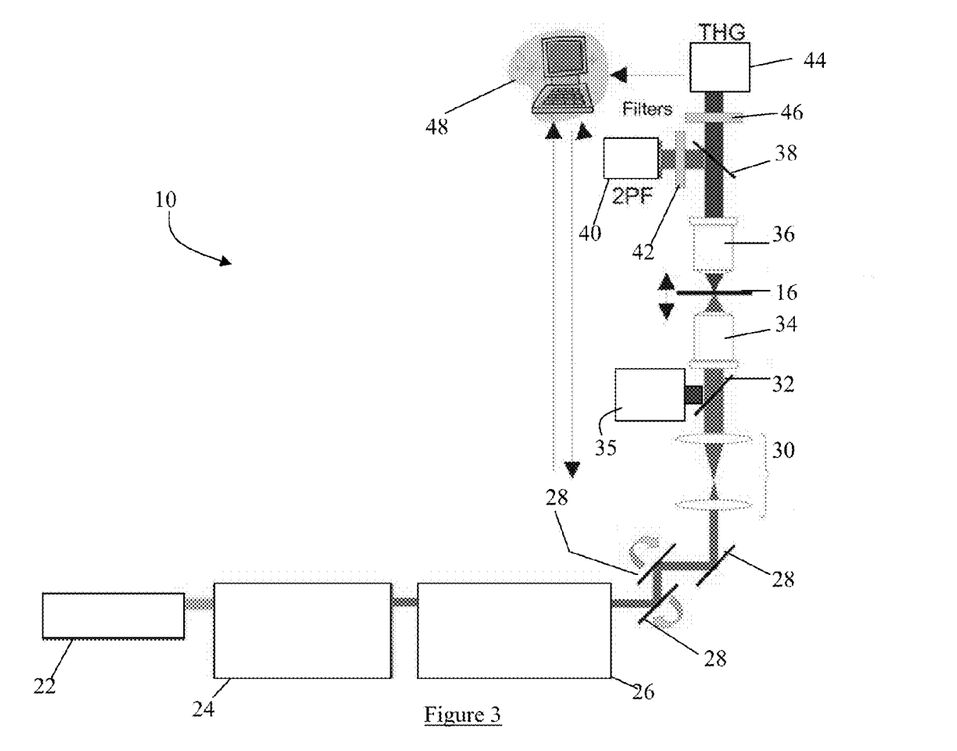
FIG. 3 illustrates a first embodiment of the system of FIG. 2.

A first embodiment of the present invention is shown in FIG. 3 where the sample 14 is a sample of blood removed from a patient, and where the haemozoin in the blood sample can be imaged. The light source 12 comprises a pump laser 22, a Ti:Sapphire laser cavity 24 and an Optical Parametric Oscillator (OPO) 26. Femtosecond laser pulses are produced inside the Ti:Sapphire laser cavity 24 and the wavelength of the laser pulses are tuned by the OPO 26 to generate femtosecond laser pulses of infrared light of fixed wavelength, centered at approximately 1200 nm. Alternatively, a fiber laser or any other type of laser can be used. Scanning mirrors 28, a beam expander 30, a dichroic mirror 32 and a high numerical aperture microscope (excitation) objective 34 are provided for focusing the generated infrared light on the sample 14 to produce nonlinear optical effects at particular positions within the sample. Any other converger means to focus the light beam on the sample may equally be used. A THG detector 35 is provided for backscattered detection. The dichroic mirror 32 and the THG detector 35 are only required for backscattered detection and so are not essential features. Also, the excitation objective 34 and the beam expander 30 can be replaced by a lens having an equivalent function if scanning is not necessary (see embodiment of FIG. 4, for example).

The sample holder 16 for holding the blood sample 14 can include a device (not shown) for consecutively presenting individual blood cells to the generated light beam so that a plurality of blood cells are screened. The device can be based on a cell sorter or a flow cytometer, for example, having a capillary tube through which the blood cells are made to flow and on which capillary the generated infrared light is focused. One such cell sorting method is described in WO2006/084283, the contents of which are hereby incorporated by reference. Alternatively, the sample holder can hold tissue samples, or any other form of sample. Alternatively, the light beam could be made to move relative to the sample, using scanning mirrors for example.

The detector 18 includes a collection objective 36 for collecting the signal emitted by the sample 14 and a dichroic mirror 38 to split the collected light in the forward direction into a first and a second detection channel of the processor 20.

The inventors have made the surprising discovery that haemozoin in a sample emits a Third Harmonic Generation (THG) signal when the sample is excited with a light source, preferably ultrashort laser pulses. As haemozoin is produced by malaria parasites, this emitted THG signal can be used to identify the presence of a malaria parasite in the sample and also to produce images of the haemozoin in the sample. It will be appreciated that other diseases, parasites or conditions for which haemozin is a marker can also be detected using embodiments of the present invention. For example, the *Haemoproteus columbae*, *Schistosoma mansoni*, and *Echinostoma* parasites, as well as the insect *Rhodnius prolixus*, are known to produce hemozoin which can be detected by embodiments of the present invention.

The first detection channel comprises a first photomultiplier tube (PMT) 40 for detecting the THG signal from haemozoin in the blood sample 14 and a filter 42 for spectrally filtering out the remaining emitted infrared laser light. The second detection channel comprises a second photomultiplier tube 44 for detecting the two-photon excited intrinsic fluorescence (2PAF) of the red blood cells and a filter 46 for spectrally filtering out the remaining emitted infrared laser light. The processor 20 includes a computer 48 having software for analog-to-digital conversion of the signal to display images of the haemozoin and the blood cells, and for controlling the scanning mirrors.

In use, femtosecond laser pulses of infrared light of fixed wavelength are generated and are focused on the blood sample 14, preferably one blood cell at a time, to cause any haemozoin in the sample to emit a non-linear signal. The non-linear signal, together with the signal generated by the blood cells is collected and split into the first and second detection channels which filter the collected light to provide an image of the haemozoin and the blood cells.

It will be appreciated that the system 10 of the present invention need not image the haemozoin or the blood cells and may be used to simply detect the presence of malarial parasites in blood. In this case, the processor 20 of the system 10 may simply include a single photomultiplier tube or the like, for detecting the THG signal from any haemozoin in the blood sample and an alert or display means for indicating the presence of haemozoin, and hence malaria, in the sample. The alert or display means may include a device for producing a sound or visual alarm. The system can be adapted to indicate the level of malaria infection by counting the haemozoin signals in a known volume of blood.

Figure 4:
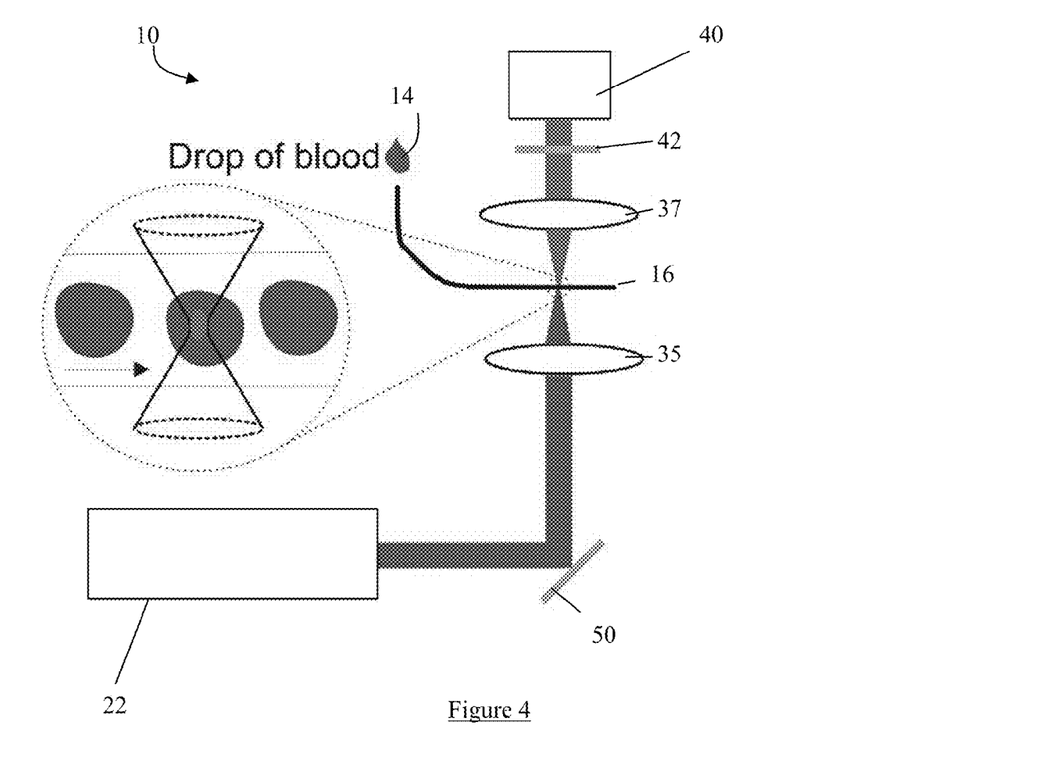
FIG. 4 illustrates a second embodiment of the system of FIG. 2.

A second embodiment of the present invention is shown in FIG. 4, which differs from the embodiment of FIG. 3 in that the system 10 only has a haemozoin detection capability rather than having the imaging capability of the first embodiment. Therefore, instead of the scanning mirrors 28 of the first embodiment, there is provided a single mirror 50. Also, the system of FIG. 4 includes only a single detector comprising a third harmonic generation photomultiplier tube 40. Furthermore, instead of the excitation and collective objectives 34, 36 and the beam expander 30, there is provided lenses 35, 37 which may or may not be objectives. It will be appreciated that the mirror 50 is not required when the light source is aligned with the lens 35.

In another embodiment (not shown), the excitation objective 34 of FIG. 3 or the lens 35 of FIG. 4 is replaced by an axicon. This can provide a deeper field of view and enable the evaluation of a sample in three dimensions.

From another aspect of the invention, a device 100 is provided incorporating the features of any of the system embodiments described above. In a first embodiment of the device 100, illustrated in FIG. 5, the device 100 is a portable device for in vivo use incorporating the light source 12 and the detector 18 within a housing 102. The device 100 may be provided with its own power source (not shown), such as a battery, or be connectable to a power source (not shown). Two compact lenses 104, 106 are provided, the first lens 104 being connectable to the light source 12 and the second lens being connectable to the detector 18. The light source 12 is a fibre laser which is connected to the first lens by fibre optic cables, or the like. The lenses 104, 106 are arranged to sandwich the sample 18 between them such that the first lens 104 transmits the light signal through the sample 14 and the second lens 106 collects the scattered signal from the sample. The first and second lenses 104, 106 can be connected together by a biasing means (not shown) such as a sprung clamp. An alert means (not shown) is also included, connected to the detector 18, to indicate when haemozoin is detected in a sample. The alert means may be a visual indicator or a sound alert. This embodiment is suitable for in vivo applications where a patient's body part such as an ear lobe or tongue can be placed between the two lenses 104, 106. In this way, a malarial infection in a patient can be detected without requiring sampling of the patient's blood. The portable aspect of the device is especially useful for malaria detection in remote areas and in the field.

Figure 5:
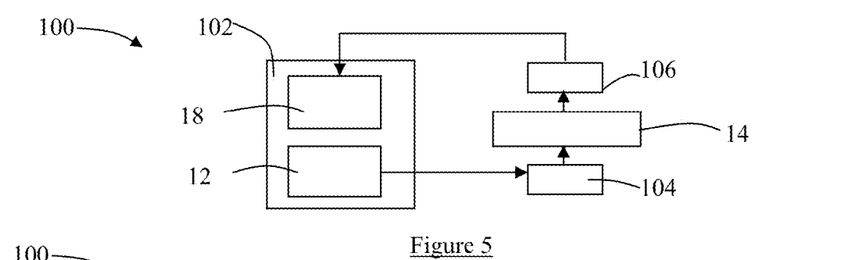
FIG. 5 illustrates a first embodiment of a device of the present invention.
Figure 6:
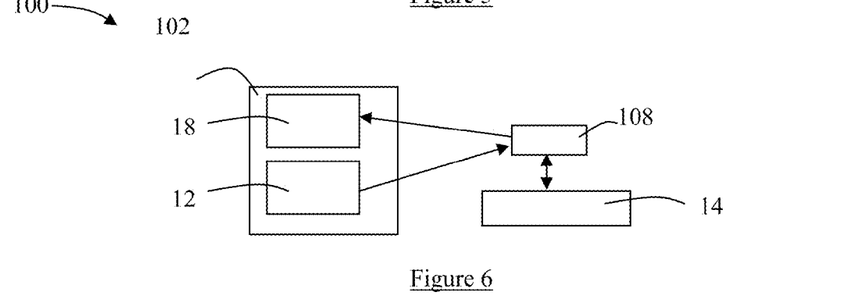
FIG. 6 illustrates a second embodiment of the device of the present invention.

A second embodiment of the device 100 is illustrated in FIG. 6 and differs from the embodiment of FIG. 5 in that a single compact lens 108 is provided to deliver the light signal to the sample 14 from the laser source and to collect a back-scattered signal and deliver it to the detector 18.

Alternatively, the device 100 of FIGS. 5 and 6 may be adapted for in vitro use by providing a sample holder between the lenses 104, 106 of FIG. 5 or adjacent the lens 108 of FIG. 6.

Figure 7:
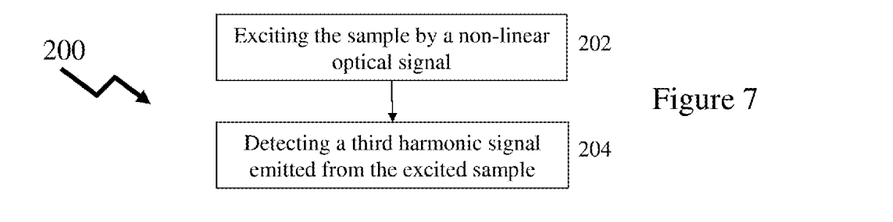
FIG. 7 illustrates one embodiment of a method of the present invention.

Referring now to FIG. 7, there is also provided a method 200 for detecting haemozoin in a sample, the method comprising a first step 202 of exciting a sample by a non-linear optical signal, and a second step of detecting a third harmonic signal emitted from the excited sample. Optionally, the detected third harmonic signal can be processed.

Any one or more of the features of the previously described embodiments may be combined in any manner. Many variations of the invention will become apparent to those skilled in the art upon review of the specification. The following example is offered by way of illustration and not by way of limitation.

EXAMPLE

Multiphoton imaging of haemozoin in red blood cells: Images of haemozoin in red blood cells were obtained using the system and method of the first embodiment described above and illustrated in FIG. 3. The light source was a Mira OPO (Coherent, Santa Clara, Calif., USA) which delivered pulses of 150 fs. Scanning was performed using VM2000 moving magnet scanning mirrors (GSI Lumonics, Moorpark, Calif., USA). The excitation and collection objectives were a 63×0.9NA water immersion lens with a 2 mm working distance and a 20×0.75NA water immersion lens with a 0.61 mm working distance, respectively (Carl Zeiss, Toronto, Canada). H7422P-40 photomultiplier tubes (Hamamatsu Photonics, Bridgewater, N.J., USA) were used for photon detection. The light was spectrally filtered using a 400/20 for THG and a 600/25 for 2PAF (Chroma, Rockingham, Vt., USA). The analog-to-digital conversion of the signal from the PMT was done using a 16 bits DAQ (National Instrument, Austin, Tex., USA).

Figure 8A:
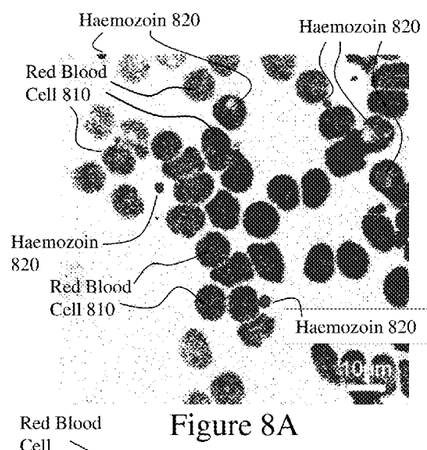
FIGS. 8(a) and (c) are multiphoton images of *Plasmodium falciparum* (malaria) infected red blood cells imaged using the system of the Example where the blue image is haemozoin and the red image is red blood cells.
Figure 8B:
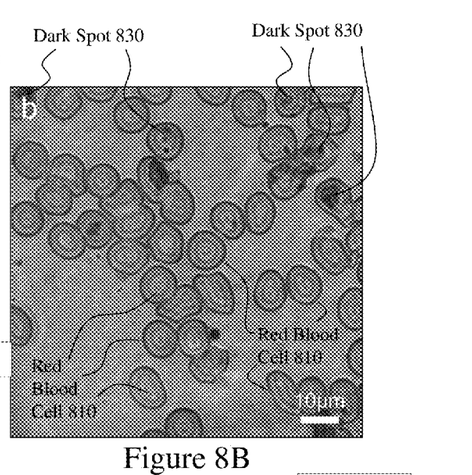
FIGS. 8(b) and (d) are optical micrographs of *Plasmodium falciparum* (malaria) infected red blood cells, of the system of the Example, imaged using thin blood film and standard Giemsa staining method for comparison.
Figure 8C:
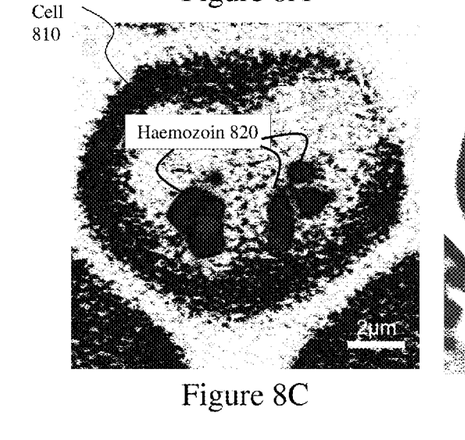
Figure 8D:
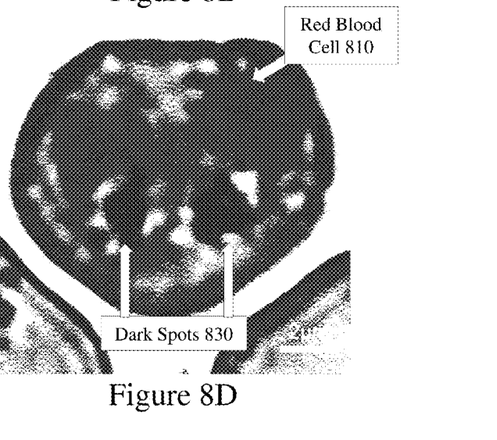

Giemsa staining: In order to confirm that the third harmonic signal was generated in malaria infected cells, smears of infected blood were stained with Giemsa to label the DNA of the malaria parasites and imaged using bright field microscopy and using THG. As can be seen in FIGS. 8(a) to 8(d) respectively, identical regions of the samples were revealed by bright field microscopy and THG images, showing a perfect overlap for the location of infected cells. The position of haemozoin 820 in FIG. 8(a) correlates with dark spots 830 in FIG. 8(b). To be able to retrieve the same area on the two microscopes, fluorescent grids produced by nonlinear lithography were used such that the red blood cells 810 can be seen to be in the same pattern. The multiphoton image (FIG. 8(a)) consisted of THG (blue emission) from haemozoin 820 and intrinsic 2PAF (red emission) from red blood cells 810. The position of haemozoin 820 in FIGS. 8(a) and 8(c) respectively correlated with dark spots 830 in FIGS. 8(b) and (d). Cells with a double infection by Plasmodium falciparum can be seen in FIGS. 8(c) and (d). FIG. 8(c) was imaged using the THG and 2PAF signal of the present invention and it overlaps with the bright field imaged dark spots of the Geimsa stained haemozoin crystals shown in FIG. 8(d).

Figure 9A:
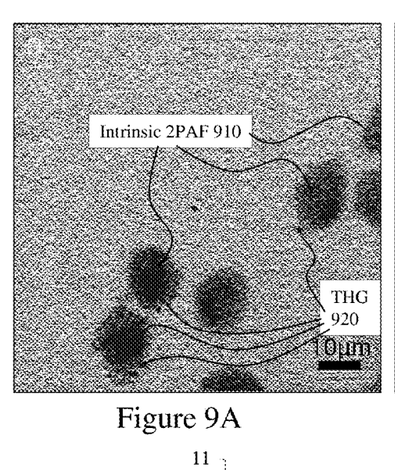
FIG. 9 illustrates Third Harmonic Generation images, consisting of THG (blue) from haemozoin and intrinsic 2PAF (green) from macrophages, of synthetic haemozoin crystals of the Example, where (a) the synthetic haemozoin crystals have been phagocytosed by macrophages and (b) the synthetic haemozoin crystals are alone on a cover glass.
Figure 9B:
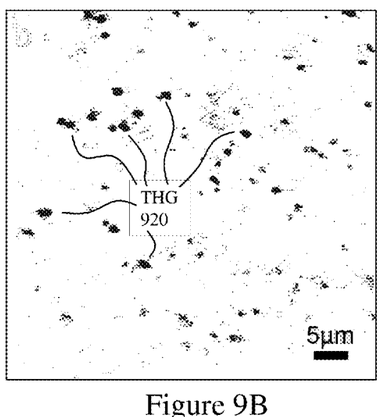

Synthesis of malaria pigment: To confirm that the THG emission was produced by malaria pigments, synthetic haemozoin crystals were imaged alone on a cover glass and also when being phagocytosed by macrophages. FIGS. 9(a) and 9(b) respectively depict images of synthetic haemozoin crystals 920. FIG. 9(a) depicting the haemozoin 920 phagocytosed by macrophages whereas FIG. 9(b) depicts the haemozoin crystals 920 alone on cover glass. The images consist of THG (blue emission) from haemozoin and intrinsic 2PAF (green emission) from macrophages.

Figure 10A:
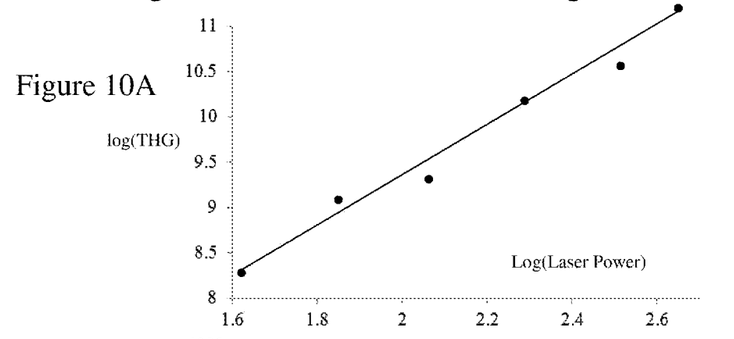
FIG. 10(a) illustrates verification of the third order dependence of the THG light with respect to the laser power.
Figure 10B:
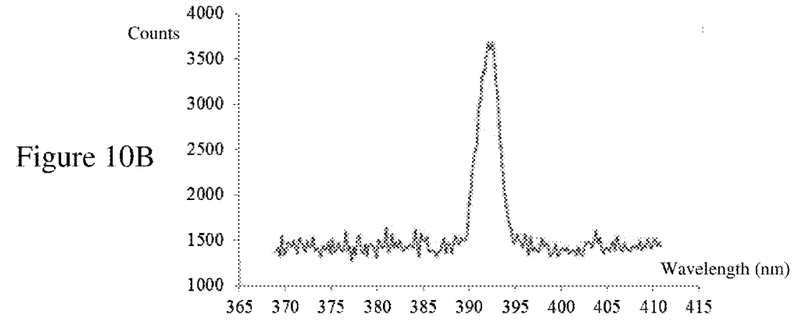
FIG. 10(b) illustrates verification that the third harmonic frequency is one third of the fundamental frequency.

Confirmation of the origin and the nature of the THG signal from haemozoin: A third order dependence of the emission on the excitation laser power was confirmed. A spectrometer was also used to check that the emission frequency was the third harmonic of the laser fundamental frequency. The nature of the signal was confirmed by verifying the third order dependence of the THG light with respect to the laser power (FIG. 10(a)) and by verifying that the third harmonic frequency was one third of the fundamental frequency (FIG. 10(b)).

Signal to noise ratio: The measured signal to noise ratio of the THG signal from the haemozoin crystals ranged from 250 to 1000, which allowed a precise localization of the haemozoin crystals in the sample (FIG. 8b). Red blood cells as well as other blood cells produce a very weak THG signal which had an intensity within the noise level. The threshold above which the THG signal can be detected depends on the laser power, the objective or lens and on the quality of the filter and the detector.

The THG images yielded signal to noise ratios ranging from 250 to 1000 for integration time of 5 µs per pixel. Considering these parameters together with the focal volume, the average hematocrit level and red blood cell dimension, it is estimated that to detect 0.0001% parasitaemia, one count would be obtained every 33 seconds. In order to obtain an average of 10 counts at the same parasitaemia level, 50 µL would be required and it would take 5.5 minutes. This estimation is conservative since based on the above experimental setup, a higher laser power and lower numerical aperture objective could easily increase the rapidity of the device by a factor of ten.

It should be appreciated that the invention is not limited to the particular embodiments described and illustrated herein but includes all modifications and variations falling within the scope of the invention as defined in the appended claims.

For example, a person skilled in the art will appreciate that any other suitable light source or light generator may be used to generate and focus pulsed infrared light to a sample of blood. Furthermore, the blood sample holder may differ from that described. It will also be appreciated that the processor may also differ from those described above. What is important is that the system includes a means for exciting a sample with incident light to emit a third harmonic signal which can be detected.

Although some embodiments of the invention have been described with respect to in vitro malaria detection, these can be adapted for in vivo malaria detection. An in vivo method has the advantage that a blood sample is not required from the patient. This can be achieved by detecting a backscattered third harmonic signal by focusing a light source on blood vessels that are close to the skin such as on the pinna in the ear or in the sclera of eyes. Also, an optical coherence topography nonlinear imaging system can be incorporated with the system of the present invention to image blood vessels or tissue structures close to the skin surface. One such optical coherence topography imaging system is described an article by Tang, S; Chen, Z and Tromberg, B J in Journal of Biomedical Optics, March/April 2006, Vol. 11(2), JBO Letters.

The invention may also have applications other than the detection of malaria in blood. For example, the invention can be used to detect structures similar to haemozoin or other structures having third harmonic generation properties and which are markers of other diseases and parasites. All documents referred to above are incorporated herein in their entirety.

The invention claimed is:

1. A method comprising:
   illuminating a predetermined portion of a biological sample with coherent radiation within a first predetermined wavelength range by at least of;
      illuminating a predetermined portion of a patient's body having blood vessels close to a surface of the patient's body, wherein the the predetermined portion is at least one of the pinna of an ear and the sclera of an eye;
      extracting a biological specimen from a patient and scanning the extracted biological specimen;
      extracting a fluid sample from a patient and processing the fluid sample with at least one of a capillary tube and a flow cytometer such that the processed sample flows through the coherent radiation with less than a predetermined number of cells within the region of illumination at any point in time; and
      extracting a biological specimen and illuminating sequentially predetermined portions of the extracted biological specimen, wherein the sequential illumination exploits an optical coherence tomography imaging system;

detecting the emission of optical radiation within a second predetermined wavelength range, the second predetermined wavelength range being that associated with third harmonic generated signals from the coherent radiation in the first predetermined wavelength range;

determining in dependence upon the detected emission of optical radiation within the second predetermined wavelength range whether the biological sample contains haemozoin.

2. The method according to claim 1 wherein, the second predetermined wavelength range is 390 nm to 395 nm.

3. A system comprising:

an optical source for illuminating a predetermined portion of a biological sample with coherent radiation within a first predetermined wavelength range, wherein illuminating a predetermined portion of the biological sample comprises at least one of:

illuminating a predetermined portion of a patient's body having blood vessels close to a surface of the patient's body, the predetermined portion is at least one of the pinna of an ear and the sclera of an eye;

extracting a biological specimen from a patient and scanning the extracted biological specimen;

extracting a fluid sample from a patient and processing the fluid sample with at least one of a capillary tube and a flow cytometer such that the processed sample flows through the coherent radiation with less than a predetermined number of cells within the region of illumination at any point in time; and extracting a biological specimen and illuminating sequentially predetermined portions of the extracted biological specimen, wherein the sequential illumination exploits an optical coherence tomography imaging system;

a first detector for detecting the emission of optical radiation within a second predetermined wavelength range, the second predetermined wavelength range being that associated with third harmonic generated signals from the coherent radiation in the first predetermined wavelength range;

a microprocessor for determining in dependence upon the detected emission of optical radiation within the second predetermined wavelength range whether the biological sample contains haemozoin; and a display for providing to a user of the system the result of the determination.

4. The system according to claim 3 wherein, the second predetermined wavelength range is 390 nm to 395 nm.

5. A method comprising:

illuminating a predetermined portion of a biological sample with coherent radiation within a first predetermined wavelength range;

detecting the emission of optical radiation within a second predetermined wavelength range, the second predetermined wavelength range being that associated with third harmonic generated signals from the coherent radiation in the first predetermined wavelength range;

determining in dependence upon the detected emission of optical radiation within the second predetermined wavelength range whether the biological sample contains haemozoin, wherein determining that the biological sample contains haemozoin is indicative that a patient providing the biological sample has at least one of:

been exposed to one of plasmodium falciparum, plasmodium vivax, plasmodium ovale, and plasmodium malariae; and been exposed to at least one of a disease, parasite, or condition for which haemozoin is a marker.

6. A method comprising:

illuminating a predetermined portion of a biological sample with coherent radiation within a first predetermined wavelength range;

detecting the emission of optical radiation within a second predetermined wavelength range, the second predetermined wavelength range being that associated with third harmonic generated signals from the coherent radiation in the first predetermined wavelength range;

determining in dependence upon the detected emission of optical radiation within the second predetermined wavelength range whether the biological sample contains haemozoin; and providing an image of the biological sample comprising first elements established in dependence upon the detected third harmonic generated signals within the second predetermined wavelength range.

7. A method comprising:

illuminating a predetermined portion of a biological sample with coherent radiation within a first predetermined wavelength range;

detecting the emission of optical radiation within a second predetermined wavelength range, the second predetermined wavelength range being that associated with third harmonic generated signals from the coherent radiation in the first predetermined wavelength range;

determining in dependence upon the detected emission of optical radiation within the second predetermined wavelength range whether the biological sample contains haemozoin;

detecting two-photon excited intrinsic fluorescence within a third predetermined wavelength range from the biological sample resulting from illumination with the coherent radiation; and providing an image of the biological sample comprising first elements established in dependence upon the detected third harmonic generated signals within the second predetermined wavelength range and second elements established in dependence upon the two-photon excited intrinsic fluorescence within the third predetermined wavelength range.

8. A system comprising:

an optical source for illuminating a predetermined portion of a biological sample with coherent radiation within a first predetermined wavelength range;

a first detector for detecting the emission of optical radiation within a second predetermined wavelength range, the second predetermined wavelength range being that associated with third harmonic generated signals from the coherent radiation in the first predetermined wavelength range;

a microprocessor for determining in dependence upon the detected emission of optical radiation within the second predetermined wavelength range whether the biological sample contains haemozoin; and a display for providing to a user of the system the result of the determination, wherein the result of the determination provided to the user is indicative that a patient providing the biological sample has at least one of:

been exposed to one of plasmodium falciparum, plasmodium vivax, plasmodium ovale, and plasmodium malariae; and been exposed to at least one of a disease, parasite, or condition for which haemozoin is a marker.

9. A system comprising:
an optical source for illuminating a predetermined portion of a biological sample with coherent radiation within a first predetermined wavelength range;
a first detector for detecting the emission of optical radiation within a second predetermined wavelength range, the second predetermined wavelength range being that associated with third harmonic generated signals from the coherent radiation in the first predetermined wavelength range;
a microprocessor for determining in dependence upon the detected emission of optical radiation within the second predetermined wavelength range whether the biological sample contains haemozoin; and
a display for providing to a user of the system the result of the determination and for providing an image generated by the microprocessor of the biological sample comprising first elements established in dependence upon the detected third harmonic generated signals within the second predetermined wavelength range.

10. A system comprising:
an optical source for illuminating a predetermined portion of a biological sample with coherent radiation within a first predetermined wavelength range;
a first detector for detecting the emission of optical radiation within a second predetermined wavelength range, the second predetermined wavelength range being that associated with third harmonic generated signals from the coherent radiation in the first predetermined wavelength range;
a microprocessor for determining in dependence upon the detected emission of optical radiation within the second predetermined wavelength range whether the biological sample contains haemozoin;
a second detector for detecting two-photon excited intrinsic fluorescence within a third predetermined wavelength range from the biological sample resulting from illumination with the coherent radiation; and
a display for providing to a user of the system the result of the determination and for providing an image generated by the microprocessor of the biological sample comprising first elements established in dependence upon the detected third harmonic generated signals within the second predetermined wavelength range and second elements established in dependence upon the two-photon excited intrinsic fluorescence within the third predetermined wavelength range.

* * * * *